United States Patent [19]

Förster et al.

[11] Patent Number: 4,500,341

[45] Date of Patent: Feb. 19, 1985

[54] PHENOXYCARBOXYLIC ACID AMIDE COMPOUNDS AND HERBICIDAL COMPOSITIONS

[75] Inventors: Heinz Förster, Wuppertal; Ludwig Eue, Leverkusen; Robert R. Schmidt, Cologne, all of Fed. Rep. of Germany

[73] Assignee: Bayer Aktiengesellschaft, Leverkusen, Fed. Rep. of Germany

[21] Appl. No.: 313,698

[22] Filed: Oct. 21, 1981

Related U.S. Application Data

[63] Continuation of Ser. No. 115,453, Jan. 25, 1980, abandoned.

[30] Foreign Application Priority Data

Feb. 17, 1979 [DE] Fed. Rep. of Germany ....... 2906237

[51] Int. Cl.³ .................. A01N 37/20; A01N 43/56; C07C 103/75; C07D 231/12
[52] U.S. Cl. ........................................ 71/92; 71/88; 71/90; 71/95; 71/96; 71/108; 71/109; 71/118; 260/239 BF; 260/544 N; 544/167; 546/146; 546/164; 546/165; 546/168; 546/226; 548/200; 548/253; 548/255; 548/262; 548/341; 548/378; 548/452; 548/491; 548/510; 548/539; 560/21; 564/165; 564/166
[58] Field of Search ................. 71/118, 92, 108, 109; 548/378; 560/21; 564/166

[56] References Cited

U.S. PATENT DOCUMENTS

| 4,070,177 | 1/1978 | Nishiyama et al. | 71/108 |
| 4,093,446 | 6/1978 | Bayer et al. | 71/108 |
| 4,134,753 | 1/1979 | Horlein et al. | 560/21 |
| 4,309,562 | 1/1982 | Takahashi et al. | 71/108 |

FOREIGN PATENT DOCUMENTS

| 3295 | 8/1979 | European Pat. Off. | 71/118 |
| 7705037 | 11/1977 | Netherlands | 71/118 |

Primary Examiner—Alton D. Rollins
Attorney, Agent, or Firm—Felfe & Lynch

[57] ABSTRACT

Phenoxycarboxylic acid amide compound of the formula

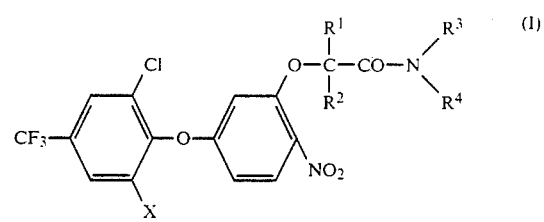

wherein
$R^1$ and $R^2$ are individually selected from hydrogen and methyl,
$R^3$ is hydrogen or alkyl with from 1 to 5 carbon atoms
$R^4$ is optionally substituted alkoxycarbonylalkyl, aminocarbonylalkyl or dialkylaminocarbonylalkyl, phenyl, or substituted phenyl wherein the substituent is at least one of the group consisting of alkyl, alkoxy or alkylthio of from 1 to 4 carbon atoms, carbalkoxy of from 2 to 4 carbon atoms, halogen, and nitro; or
$R^3$ and $R^4$, together with the adjacent nitrogen atom, form an mono- or bicyclic ring with up to 15 carbon atoms and which is optionally substituted by 1 to 3 alkyl groups of up to 4 carbon atoms each, and which ring may be partially unsaturated and/or benzofused; or a saturated mono-cyclic ring of up to 8 carbon atoms and containing a further hetero-atom selected from nitrogen, oxygen and sulfur, which ring is optionally substituted by one or two alkyl groups of up to 2 carbon atoms each; or an unsaturated 5-membered heterocyclic ring containing up to 4 ring nitrogen atoms and which ring is optionally substituted with at least one member of the group consisting of alkyl of up to 4 carbon atoms, alkoxy of up to 4 carbon atoms, alkylthio of up to 4 carbon atoms, phenyl, halogen, halomethyl, cyano, alkanoyl of up to 4 carbon atoms and carbalkoxy of from 2 to 4 carbon atoms; and
X is hydrogen or chlorine;
are outstandingly effective herbicides.

13 Claims, No Drawings

PHENOXYCARBOXYLIC ACID AMIDE COMPOUNDS AND HERBICIDAL COMPOSITIONS

This is a continuation application of Ser. No. 115,453 filed Jan. 25, 1980, abandoned.

The present inventon relates to certain new phenoxycarboxylic acid amide compounds, to herbicidal compositions containing them and to methods of combating weeds utilizing such compounds.

It is already known that certain phenoxycarboxylic acid derivatives have herbicidal properties. Thus, for example, 5-(2-chloro-4-trifluoromethylphenoxy)-2-nitro-α-phenoxy-propionic acid methyl ester and 5-(2-chloro-4-trifluoromethyl-phenoxy)-2-nitro-α-phenoxy-propionic acid ethyl ester can be used for combating weeds (see U.S. Pat. No. 4,093,446 and DE-OS (German Published Specification) No. 2,311,638). The action of these substances is good, both when they are used in accordance with the pre-emergence process and when they are used in accordance with the post-emergence process. However, their disadvantage is that some problem broad-leaved weeds and graminaceous weeds are not always completely combated.

The present invention now provides, as new compounds, the phenoxycarboxylic acid amides of the formula

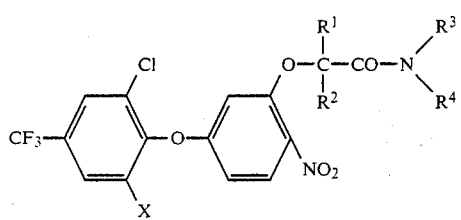

wherein
$R^1$ and $R^2$ are individually selected from hydrogen and methyl,
$R^3$ is hydrogen or alkyl with from 1 to 5 carbon atoms
$R^4$ is optionally substituted alkoxycarbonylalkyl, aminocarbonylalkyl or dialkylaminocarbonylalkyl, phenyl, or substituted phenyl wherein the substituent is at least one of the group consisting of alkyl, alkoxy or alkylthio of from 1 to 4 carbon atoms, carbalkoxy of from 2 to 4 carbon atoms, halogen and nitro; or
$R^3$ and $R^4$, together with the adjacent nitrogen atom, form an optionally partially unsaturated and/or benzo-fused monocyclic or bicyclic ring with up to 15 carbon atoms which is optionally substituted by 1 to 3 alkyl groups with in each case 1 to 4 carbon atoms, or a saturated monocyclic ring which has up to 8 carbon atoms, contains a further heteroatom selected from nitrogen, oxygen and sulphur atoms and is optionally substituted by 1 or 2 alkyl groups with in each case 1 to 2 carbon atoms, or an unsaturated 5-membered heterocyclic ring which contains up to 4 ring nitrogen atoms and is optionally substituted by $C_1$–$C_4$-alkyl, $C_1$–$C_4$-alkoxy, $C_1$–$C_4$-alkylthio, phenyl, halogen, halomethyl, cyano, $C_1$–$C_4$-akoanoyl or $C_2$–$C_4$-carbalkoxy, and
X represents hydrogen or chlorine.

It has been found that the phenoxycarboxylic acid amides of the formula (I) have powerful herbicidal properties.

Preferably, in formula (I),
$R^1$ represents hydrogen,
$R^2$ represents methyl,
$R^3$ represents hydrogen or alkyl with 1 to 3 carbon atoms, and
$R^4$ represents alkoxy-carbonylmethyl with 1 to 4 carbon atoms in the alkoxy group, aminocarbonylmethyl or di-$C_{1-4}$-alkylaminocarbonylmethyl, or represents phenyl which optionally carries one or two substituents selected from alkyl with 1 to 3 carbon atoms, alkoxy with 1 to 3 carbon atoms, methylthio, chlorine and nitro, or
$R^3$ and $R^4$, together with the adjacent nitrogen atom, represent pyrrolidyl or morpholinyl, in either case optionally substituted by 1 or 2 methyl or ethyl groups, or represent piperidyl, indolyl, tetrahydroindolyl, perhydroindolyl, tetrahydroquinolyl, tetrahydroisoquinolyl, perhydroquinolyl, perhydroisoquinolyl, perhydrothiazolyl or perhydroazepinyl, in each case optionally substituted by 1 to 3 methyl or ethyl groups, or represent pyrrolyl, pyrazolyl, imidazolyl, 1,2,4-triazol-1-yl, 1,2,3-triazol-1-yl, 1,3,4-triazol-1-yl or 1,2,3,4-tetrazol-1-yl, in each case optionally substituted by $C_1$–$C_3$-alkyl, $C_1$–$C_3$-alkoxy, $C_1$–$C_3$-alkylthio, phenyl, chlorine, bromine, iodine, trifluoromethyl, cyano, acetyl, carbomethoxy or carbethoxy; and
X represents hydrogen or chlorine.

The invention also provides a process for the preparation of a phenoxycarboxylic acid amide of the formula (I) in which a phenoxycarboxylic acid chloride of the general formula

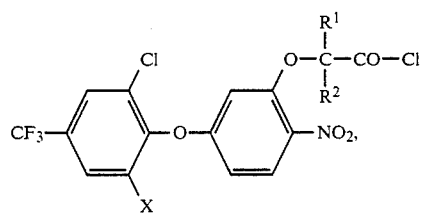

in which $R^1$, $R^2$ and X have the meanings indicated above, is reacted with a compound of the general formula

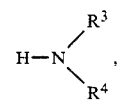

in which $R^3$ and $R^4$ or the radical

have the meanings indicated above,
if appropriate in the presence of an acid acceptor and if appropriate in the presence of a diluent.

Surprisingly, the phenoxycarboxylic acid amides according to the invention exhibit a considerably better herbicidal action than the compounds 5-(2-chloro-4-trifluoromethylphenoxy)-2-nitro-α-phenoxy-propionic acid methyl ester and 5-(2-chloro-4-trifluoromethyl-phenoxy)-2-nitro-α-phenoxy-propionic acid ethyl ester, which are known from the state of the art and are active compounds of the same type of action which are very closely related chemically. It should be noted in particular that the phenoxycarboxylic acid amides of the present invention are more advantageous in the combating of problem broadleaved weeds and graminaceous weeds, for example Galium and Gyperus, than the previously known substances mentioned above. The active compounds according to the invention thus represent a valuable enrichment of the art.

If 5-(2,6-dichloro-4-trifluoromethyl-phenoxy)-2-nitro-α-phenoxy-propionic acid chloride and 1,2,4-triazole are used as starting materials, the course of the reaction in the process according to the invention can be represented by the following equation:

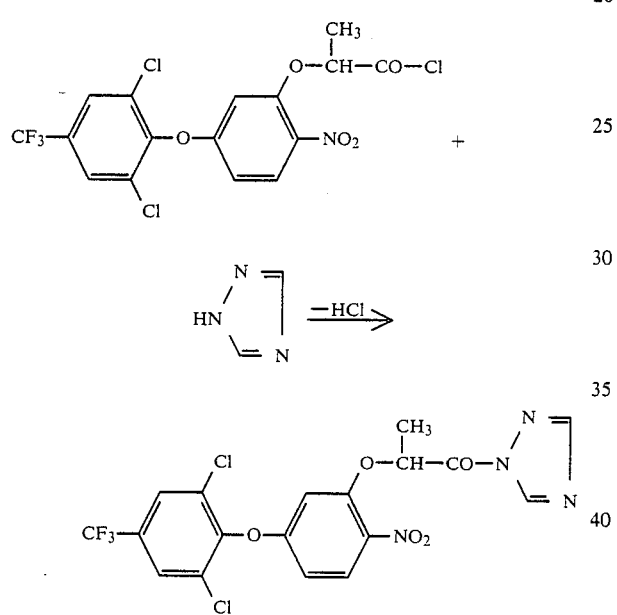

The formula (II) provides a general definition of the phenoxycarboxylic acid chlorides required as starting materials in carrying out the process according to the invention. In this formula, $R^1$, $R^2$ and X preferably have those meanings which have already been mentioned as preferred in connection with the description of the substances of the formula (I).

Examples of the phenoxycarboxylic acid chlorides of the formula (II) which may be mentioned are: 5-(2-chloro-4-trifluoromethyl-phenoxy)-2-nitro-α-phenoxy- and 5-(2,6-dichloro-4-trifluoromethyl-phenoxy)-2-nitro-α-phenoxy-propionyl chloride.

The phenoxycarboxylic acid chlorides of the formula (II) are known, or they can be prepared in a simple manner by customary methods (see U.S. Pat. No. 4,093,446). Thus, a phenoxycarboxylic acid chloride of the formula (II) can be synthesized by a process in which a phenoxycarboxylic acid of the general formula

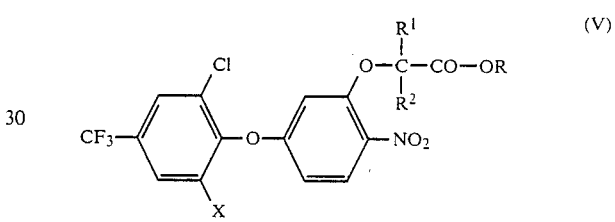

in which $R^1$, $R^2$ and X have the meanings indicated above, is reacted with a chlorinating agent, for example thionyl chloride, if appropriate using a diluent, for example benzene or ethylene chloride, at a temperature between 10° and 100° C. and, when the reaction has ended, highly volatile components are removed by distillation.

The phenoxycarboxylic acids of the formula (IV) are likewise known, or they can be prepared in a simple manner by customary methods (see U.S. Pat. No. 4,093,446). Thus, a phenoxycarboxylic acid of the formula (IV) can be synthesized by a process in which a phenoxycarboxylic acid ester of the general formula $$\begin{array}{c}R^1\\|\\O-C-CO-OR\\|\\R^2\end{array} \quad (V)$$

in which
$R^1$, $R^2$ and X have the meanings indicated above and
R represents alkyl (especially methyl or ethyl), is reacted with an aqueous alkali metal hydroxide solution, preferably with sodium hydroxide solution or potassium hydroxide solution, which is optionally diluted with an organic solvent, for example methanol, ethanol or dioxan, at a temperature between 20° and 100° C.

Examples of the phenoxycarboxylic acids of the formula (IV) which may be mentioned are: 5-(2-chloro-4-trifluoromethyl-phenoxy)-2-nitro-α-phenoxy- and 5-(2,6-dichloro-4-trifluoromethyl-phenoxy)-2-nitro-α-phenoxypropionic acid.

The phenoxycarboxylic acid esters of the formula (V) are likewise known, or they can be prepared in a simple manner by customary methods (see U.S. Pat. No 4,093,446). Thus a phenoxycarboxylic acid ester of the formula (V) can be synthesised by a process in which a phenol derivative of the general formula

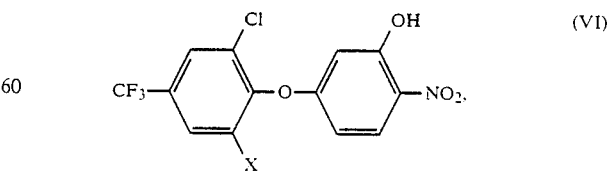

in which X has the meaning indicated above, or the sodium or potassium salt of the phenol derivative, is reacted with an α-halogeno-carboxylic acid ester of the general formula

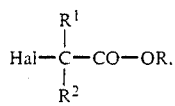

$$\text{Hal} - \underset{R^2}{\overset{R^1}{\underset{|}{\overset{|}{C}}}} - \text{CO} - \text{OR}. \qquad (\text{VII})$$

in which

R¹ and R² have the meanings indicated above,
R represents alkyl (especially methyl or ethyl) and
Hal represents chlorine or bromine,
if appropriate in the presence of an acid-binding agent, for example sodium methylate or potassium carbonate, and if appropriate using a polar diluent, for example methanol, acetonitrile or sulpholane, at a temperature between 20° and 100° C.

Examples of the phenoxycarboxylic acid esters of the formula (V) which may be mentioned are: 5-(2-chloro-4-trifluoromethyl-phenoxy)-2-nitro-α-phenoxy- and 5-(2,6-dichloro-4-trifluoromethyl-phenoxy)-2-nitro-α-phenoxy-propionic acid methyl ester and ethyl ester.

The phenol derivatives of the formula (VI) are known (see U.S. Pat. No. 4,093,446). Examples of the phenol derivatives of the formula (VI) which may be mentioned are: 5-(2-chloro-4-trifluoromethyl-phenoxy)-2-nitro-phenol and 5-(2,6-dichloro-4-trifluoromethyl-phenoxy)-2-nitro-phenol.

The α-halogeno-carboxylic acid esters of the formula (VII) are also known. Examples of these which may be mentioned are: α-chloro-propionic acid methyl ester and ethyl ester and α-bromo-propionic acid methyl ester and ethyl ester.

The formula (III) provides a general definition of compounds also required as starting materials in the process according to the invention. In this formula, R³ and R⁴ preferably have those meanings which have already been mentioned as preferred for these radicals in connection with the description of the phenoxycarboxylic acid amides of the formula (I).

The compounds of the formula (III) are known. Specific examples which may be mentioned are: aminoacetic acid methyl ester, ethyl ester, propyl ester and butyl ester, aniline, 2-methyl-, 3-methyl- and 4-methyl-aniline, 4-methoxy-, 3,4-dimethoxy- and 4-methylthio-aniline, 2-chloro-, 3-chloro- and 4-chloro-aniline, 2,4-dichloro-, 3,4-dichloro- , 2,5-dichloro- and 3,5-dichloro-aniline, 2-nitro-, 3-nitro- and 4-nitro-aniline and 3-nitro-6-methyl-aniline; N-methyl-aniline, 2-methyl-, 3-methyl- and 4-methyl-N-methyl-aniline, 4-methoxy-, 3,4-dimethoxy- and 4-methyl-thio-N-methyl-aniline, 2-chloro-, 3-chloro- and 4-chloro-N-methyl-aniline, 2,4-dichloro-, 3,4-dichloro-, 2,5-dichloro- and 3,5-dichloro-N-methyl-aniline, 2-nitro-, 3-nitro- and 4-nitro-N-methyl-aniline and 3-nitro-6-methyl-N-methyl-aniline; N-ethyl-aniline, 2-methyl-, 3-methyl- and 4-methyl-N-ethyl-aniline, 4-methoxy-, 3,4-dimethoxy- and 4-methyl-thio-N-ethyl-aniline and 2-chloro-, 3-chloro- and 4-chloro-N-ethyl-aniline; 2,4-dichloro-, 3,4-dichloro-, 2,5-dichloro- and 3,5-dichloro-N-ethyl-aniline, 2-nitro-, 3-nitro- and 4-nitro-N-ethyl-aniline and 3-nitro-6-methyl-N-ethyl-aniline; N-n-propyl-aniline, 2-methyl-, 3-methyl- and 4-methyl-N-n-propyl-aniline, 4-methoxy-, 3,4-dimethoxy- and 4-methylthio-N-n-propyl-aniline, 2-chloro-, 3-chloro- and 4-chloro-N-n-propyl-aniline, 2,4-dichloro-, 3,4-dichloro-, 2,5-dichloro- and 3,5-dichloro-N-n-propyl-aniline and 2-nitro-, 3-nitro- and 4-nitro-N-n-propyl-aniline; 3-nitro-6-methyl-N-n-propyl-aniline; N-iso-propyl-aniline, 2-methyl-, 3-methyl- and 4-methyl-N-iso-propyl-aniline, 4-methoxy-, 3,4-dimethoxy- and 4-methyl-thio-N-iso-propyl aniline, 2-chloro-, 3-chloro- and 4-chloro-N-iso-propyl-aniline, 2,4-dichloro-, 3,4-dichloro-, 2,5-dichloro- and 3,5-dichloro-N-iso-propyl-aniline, 2-nitro, 3-nitro- and 4-nitro-N-iso-propyl-aniline and 3-nitro-6-methyl-N-iso-propyl-aniline; pyrrolidine, 2-methyl-pyrrolidine, morpholine, 2,6-dimethyl-morpholine, piperidine, 2-methyl- and 4-methyl-piperidine, 2,4-dimethyl-piperidine, 2,4,6-trimethyl-piperidine, 2-ethyl-piperidine, 2-methyl-5-ethyl-piperidine, tetrahydroindoline, 2-methyl-tetrahydroindoline, 2,3,3-trimethyl-tetrahydroindoline, perhydroindoline, 2-methyl-perhydroindoline, 2,2-dimethyl-perhydroindoline, tetrahydroquinoline, perhydroquinoline, 4-methyl- and 6-methyl-perhydroquinoline, tetrahydroisoquinoline, perhydrothiazole and perhydroazepine(hexamethyleneimine); pyrrole, 2,4-dimethyl- and 2,5-dimethyl-pyrrole, tetramethylpyrrole, 3(5)-methylpyrazole, 4-methylpyrazole, 3(5)-ethylpyrazole, 4-ethylpyrazole, 3(5)-isopropylpyrazole, 4-isopropylpyrazole, 3,5-dimethylpyrazole, 3,5-dimethyl-4-acetylpyrazole, 3,4,5-trimethylpyrazole, 3(5)-phenylpyrazole, 4-phenylpyrazole, 3,5-diphenylpyrazole, 3(5)-phenyl-5-(3)-methylpyrazole, 3(5)-chloropyrazole, 4-chloropyrazole, 4-bromopyrazole, 4-iodopyrazole, 3,4,5-trichloropyrazole, 3,4,5-tribromopyrazole, 3,5-dimethyl-4-chloropyrazole, 3,5-dimethyl-4-bromopyrazole, 4-chloro-3(5)-methylprazole, 4-bromo-3(5)-methylpyrazole, 4-methyl-3,5-dichloropyrazole, 3(5)-methyl-4,5(3)-dichloropyrazole, 3(5)-chloro-5(3)-methylpyrazole, 4-methoxypyrazole, 3(5)-methyl-5(3)-methoxypyrazole, 3(5)-ethoxy-4,5(3)-dimethylpyrazole, 3(5)-methyl-5(3)-trifluoromethylpyrazole, 3,5-bis-trifluoromethylpyrazole, 3(5)-methyl-5(3)-carbethoxypyrazole, 3,5-bis-carbethoxypyrazole, 3,4,5-tris-carbethoxypyrazole, 3(5)-methyl-5(3)-methylthio-4-carbethoxypyrazole, 4-methyl-3,5-bis-carbethoxypyrazole, 4-cyanopyrazole, 4-methoxy-3,5-dichloropyrazole, imidazole, 2,4,5-trichloroimidazole, 1,2,4-triazole, 3(5)-methyl-1,2,4-triazole, 3,5-dimethyl-1,2,4-triazole, 3(5)-chloro-1,2,4-triazole, 3(5)-bromo-1,2,4-triazole, 3(5)-chloro-5(3)-methyl-1,2,4-triazole, 3,5-dichloro-1,2,4-triazole, 3,5-dibromo-1,2,4-triazole, 3(5)-chloro-5(3)-cyano-1,2,4-triazole, 3(5)-chloro-5(3)-phenyl-1,2,4-triazole, 3(5)-chloro-5(3)-carbomethoxy-1,2,4-triazole, 3(5)-methylthio-1,2,4-triazole, 4(5)-methyl-1,2,3-triazole, 4,5-dimethyl-1,2,3-triazole, 4(5)-phenyl-1,2,3-triazole, 4(5)-chloro-1,2,3-triazole,1,2,3-triazol-4(5)-yl-carboxylic acid ethyl ester, 1,2,3-triazol-4,5-yl-dicarboxylic acid dimethyl ester, 5-methyltetrazole, 4-chlorotetrazole, tetrazolyl-5-carboxylic acid ethyl ester, 1,3,4-triazole and 1,2,3,4-tetrazole.

The process according to the invention is preferably carried out using a suitable solvent or diluent. Possible solvents or diluents are virtually any of the inert organic solvents. These include, as preferences, aliphatic and aromatic, optionally chlorinated hydrocarbons, such as benzine, benzene, toluene, xylene, methylene chloride, chloroform, carbon tetrachloride, chlorobenzene and o-dichlorobenzene; ethers, such as diethyl ether, dibutyl ether, tetrahydrofuran and dioxan; ketones, such as acetone, methyl ethyl ketone, methyl isopropyl ketone and methyl isobutyl ketone; nitriles, such as acetonitrile and propiontrile; esters, such as methyl acetate or ethyl acetate, and formamides, such as dimethylformamide.

Any of the customary acid-binding agents can be used as the acid acceptor. Alkali metal carbonates and alcoholates, such as sodium carbonate and potassium carbonate and sodium methylate or ethylate and potassium methylate or ethylate, and furthermore aliphatic, aromatic or heterocyclic amines, for example triethylamine, trimethylamine, dimethylaniline, dimethylbenzylamine and pyridine, have proved particularly suitable.

Instead of the above-mentioned acid acceptors, the reactants of the formula (III) can also function as acid-binding agents, and in this case are to be employed in an appropriate excess.

The reaction temperature can be varied within a substantial range. In general, the reaction is carried out at from $-20°$ to $+100°$ C., preferably at from $0°$ to $50°$ C. The process according to the invention is in general carried out under normal pressure.

In carrying out the process according to the invention, 1 to 3 moles, preferably 1 to 1.5 moles, of a compound of the formula (III) and, if appropriate, 1 to 2 moles of acid-binding agent are generally employed per mole of phenoxycarboxylic acid chloride of the formula (II). The reaction is in general carried out in a suitable diluent and the reaction mixture is stirred at the required temperature for several hours. Isolation of the reaction products of the formula (I) according to the invention is effected by customary methods. In general, when the reaction has ended, the reaction mixture is diluted with a water-immiscible solvent, for example toluene, and washed successively with dilute hydrochloric acid or sulphuric acid, dilute sodium hydroxide solution and water. The nonaqueous phase is then dried, filtered and freed from solvent by distillation under reduced pressure.

In general, the products are obtained in a solid form and can be purified by recrystallization. They are characterised by their melting point.

The active compounds according to the invention influence plant growth and can therefore be used as defoliants, desiccants, agents for destroying broad-leaved plants, germination inhibitors and, especially, as weed-killers. By "weeds" in the broadest sense there are meant plants growing in places where they are not desired.

Whether the compounds according to the invention act as total herbicides or selective herbicides depends essentially on the amount used.

The active compounds according to the present invention may be used, for example, to combat the following plants:

dicotyledon weeds of the genera Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduss, Sonchus, Rorippa, Rotala, Lindernia, Lamium, Veronica, Abutilon, Emex, Datura, Viola, Galeopsis, Papaver, Centaurea and Solanum; and monocotyldeon weeds of the genera Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleoncharis, Scirpus, Paspalum, Ischaemum, Sphenoclea, Dactyloctenium, Agrostis, Alopecurus and Apera.

The active compounds according to the present invention may be used, for example, as selective herbicides in the following cultures:

dicotyledon cultures of the genera Gossypium, Glycine, Beta, Daucus, Phaseolus, Pisum, Solanum, Linum, Ipomoea, Vicia, Nicotiana, Lycopersicon, Arachis, Brasica, Lactuca, Cucumis and Cucurbita; and monocotyledon cultures of the genera Cryza, Zea, Triticum, Hordeum, Avena, Secale, Sorghum, Panicum, Saccharum, Ananas, Asparagus and Allium.

However, the use of the active compounds according to the invention is in no way restricted to these genera but also embraces other plants, in the same way.

Depending on the concentrations, the compounds can be used for the total combating of weeds, for example on industrial terrain and railway tracks and on paths and square with or without trees. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cacao plantations, soft fruit plantings and hopfields, and for the selective combating of weeds in annual cultures.

The active compounds can be converted into the customary formulations, such as solutions, emulsions, suspensions, powders, foams, pastes, granules, natural and synthetic materials impregnated with active compound, and very fine capsules in polymeric substances.

These formulations may be produced in known manner, for example by mixing the active compounds with extenders, that is to say liquid or solid diluents or carriers, optionally with the use of surface-active agents, and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used non-ionic and anionic emulsifiers, such as polyoxethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention, as such or in the form of their formulations, can also be used for combating weeds, as mixtures with other herbicides, finished formulations or tank mixing being possible. Mixtures with other active compounds, such as fungicides, insecticides, acaricides, nematicides, bird repellants, growth factors, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They are preferably applied before emergence of the plants, that is to say by the pre-emergence method. They can also be incorporated into the soil before sowing.

The amount of active compound used can vary within a substantial range. It depends essentially on the nature of the desired effect. In general, the amounts used are from 0.05 and 10 kg of active compound per hectare, preferably between 0.1 and 5 kg/ha.

The present invention also provides a herbicidal composition containing as active ingredient a compound of the present invention in admixture with a solid diluent or carrier or in admixture with a liquid diluent or carrier containing a surface-active agent.

The present invention also provides a method of combating weeds which comprises applying to the weeds, or to a habitat thereof, a compound of the present invention alone or in the form of a composition containing as active ingredient a compound of the present invention in admixture with a diluent or carrier.

The present invention further provides crops protected from damage by weeds by being grown in areas in which immediately prior to and/or during the time of the growing a compound of the present invention was applied alone or in admixture with a diluent or carrier.

It will be seen that the usual methods of providing a harvested crop may be improved by the present invention.

The herbicidal activity of the compounds of this invention is illustrated by the following biotest Examples.

In these Examples, the compounds according to the present invention are each identified by the number (given in brackets) of the corresponding preparative Example, which will be found later in this specification.

The known comparison compounds are identified as follows:

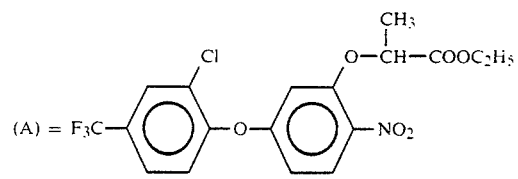

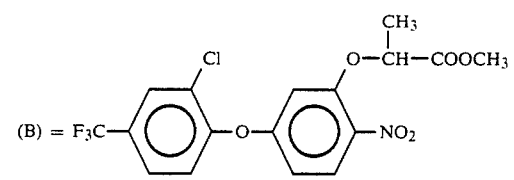

EXAMPLE A

Pre-emergence test

Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

Seeds of the test plants were sown in normal soil and, after 24 hours, watered with the preparation of the active compound. It was expedient to keep constant the amount of water per unit area. The concentration of the active compound in the preparation was of no importance, only the amount of active compound applied per unit area being decisive. After three weeks, the degree of damage to the plants was determined in % damage in comparison to the development of the untreated control. The figures denoted:

0% = no action (like untreated control)
100% = total destruction

In this test, the active compound (3) exhibited a better action against Cyperus than the known comparison substance (A).

EXAMPLE B

Pre-emergence test

Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

Seeds of the test plants were sown in normal soil and, after 24 hours, watered with the preparation of the active compound. It was expedient to keep constant the amount of water per unit area. The concentration of the active compound in the preparation was of no importance, only the amount of active compound applied per unit area being decisive. After three weeks, the degree of damage to the plants was determined in % damage in comparison to the development of the untreated control. The figures denoted:

0% = no action (like untreated control)
100% = total destruction

In this test, the active compound (3) exhibited a better action against Galium than the known comparison substance (B).

PREPARATIVE EXAMPLES

Example 1

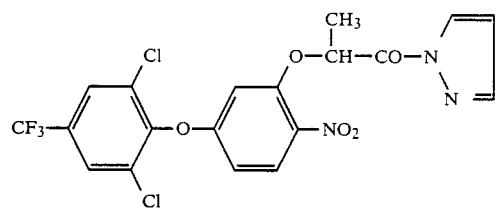

A solution of 22.9 g (50 mmol) of 5-(2,6-dichloro-4-trifluoromethylphenoxy)-2-nitro-α-phenoxy-propionyl chloride in 40 ml of toluene was added dropwise to a solution, cooled to 0° to 50° C., of 3.6 g (53 mmol) of pyrazole and 5.6 g (55 mmol) of triethylamine in 70 ml of toluene. The reaction mixture was stirred overnight at room temperature, diluted with toluene, washed until neutral, dried and filtered and the filtrate was concentrated. 20 g (81.6% of theory) of 5-(2,6-dichloro-4-trifluoromethyl-phenoxy)-2-nitro-α-phenoxy-propionic acid pyrazolide were obtained in the form of yellow crystals of melting point 144° C.

The compounds of the formula (I) listed in Table 1 below were prepared analogously to Example 1:

TABLE 1

| Example No. | X | R¹ | R² | NR³R⁴ | Melting point (° C.) |
|---|---|---|---|---|---|
| 2 | H | H | $CH_3$ | -N-N=C(CH₃)-CH=C(CH₃) | 97 |
| 3 | H | H | $CH_3$ | -N-N=CH-CH=CH (pyrazolyl) | 115 |
| 4 | H | H | $CH_3$ | -NH-C₆H₅ | 106 |
| 5 | H | H | $CH_3$ | -N(CH₃)-C₆H₅ | 112 |
| 6 | H | H | $CH_3$ | -N(piperidinyl-CH₃) | 104 |
| 7 | H | H | $CH_3$ | -NH-CH₂-CO-OC₂H₅ | 82 |
| 8 | Cl | H | $CH_3$ | -NH-CH₂-CO-OC₂H₅ | 119 |

The phenoxycarboxylic acid chlorides to be used as starting materials could be prepared, for example, as follows:

Example II-1

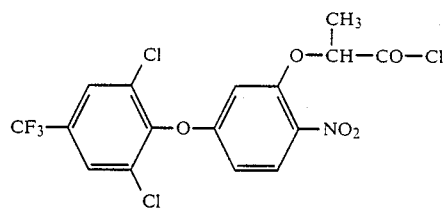

9.7 g (82 mmol) of thionyl chloride were added dropwise to a solution of 30 g (68 mmol) of 5-(2,6-dichloro-4-trifluoromethyl-phenoxy)-2-nitro-α-phenoxy-propionic acid and 0.5 ml of dimethylformamide in 100 ml of 1,2-dichloroethane at room temperature. The mixture was heated under reflux for 4 hours. Active charcoal was added, the mixture was filtered and the filtrate was concentrated. After digesting the oily residue with 100 ml of ligroin, 26.2 g (84% of theory) of 5-(2,6-dichloro-4-trifluoromethylphenoxy)-2-nitro-α-phenoxy-propionyl chloride were obtained in the form of yellow crystals of melting point 92° C.

The phenoxycarboxylic acids required as precursors could be prepared, for example, as follows:

Example IV-1

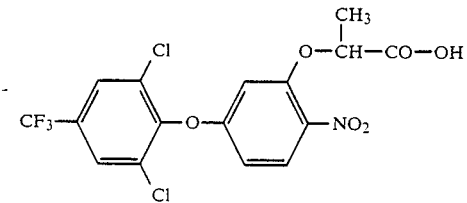

135 g (0.3 mol) of 5-(2,6-dichloro-4-trifluoromethyl-phenoxy)-2-nitro-α-phenoxy-propionic acid methyl ester and 30 ml of concentrated aqueous sodium hydroxide solution were stirred in 400 ml of acetonitrile and 150 ml of water at 20° C. for 24 hours. The solution was concentrated, the residue was taken up in 500 ml of water and the aqueous mixture was acidified with 50 ml of concentrated hydrochloric acid. 93 g (71% of theory) of 5-(2,6-dichloro-4-trifluoromethyl-phenoxy)-2-nitro-α-phenoxy-propionic acid were obtained in the form of pale yellow crystals of melting point 146° C. (after recrystallization from toluene/cyclohexane).

The phenoxycarboxylic acid esters required as precursors could be prepared, for example, as follows:

Example V-1

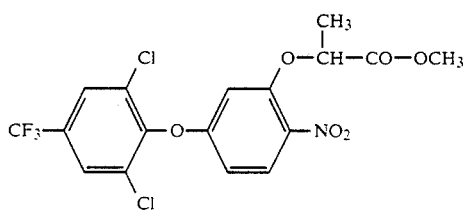

40 g (0.24 mol) of α-bromo-propionic acid methyl ester were added dropwise to a mixture, warmed to 50° C., of 73.6 g (0.2 mol) of 5-(2,6-dichloro-4-trifluoromethylphenoxy)-2-nitro-phenol, 32 g of potassium carbonate and 200 ml of acetonitrile. The reaction mixture was heated under reflux for 5 hours and then poured into 1 liter of water and the aqueous mixture was extracted with 1 liter of toluene. The toluene phase was washed with 300 ml aqueous sodium hydroxide solution and then with 500 ml of water. After distilling off the solvent in vacuo, 74 g (81% of theory) of 5-(2,6-dichloro-4-trifluoromethylphenoxy)-2-nitro-α-phenoxy propionic acid methyl ester were obtained as an oil which crystallized on adding methanol, the crystals having a melting point of 78° C.

It will be understood that the specification and examples are illustrative but not limitative of the present invention and that other embodiments within the spirit and scope of the invention will suggest themselves to those skilled in the art.

What is claimed is:

1. Phenoxylcarboxylic acid amide compound of the formula

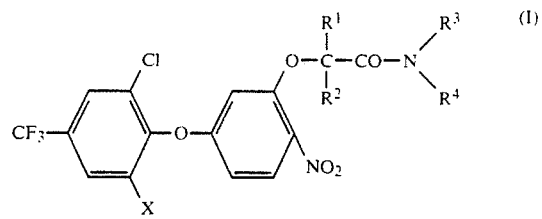

wherein
$R^1$ is hydrogen,
$R^2$ is methyl,
$R^3$ is hydrogen,
$R^4$ is alkoxycarbonylmethyl with 1 to 4 carbon atoms in the alkoxyl group or
$R^3$ and $R^4$ together with the adjacent nitrogen atom are pyrazolyl or pyrazolyl which is substituted by one or two methyl groups and
X is hydrogen or chlorine.

2. Phenoxycarboxylic acid amide compound as claimed in claim 1 wherein $R^4$ is alkoxycarbonylmethyl.

3. Phenoxycarboxylic acid amide compound as claimed in claim 1 wherein X is hydrogen.

4. Phenoxycarboxylic acid amide compound as claimed in claim 1 wherein X is chlorine.

5. Phenoxycarboxylic acid amide compound designated 5-(2-chloro-4-trifluoromethylphenoxy)-2-nitro-α-phenoxy-propionic acid pyrazolide.

6. Phenoxycarboxylic acid amide compound as claimed in claim 1 designated 5-(2-chloro-4-trifluoromethyl-phenoxy)-2-nitro-α-phenoxy-propionic acid N-(ethoxycarbonylmethyl)amide.

7. Phenoxycarboxylic acid amide compound as claimed in claim 1 designated 5-(2,6-dichloro-4-trifluoromethyl-phenoxy)-2-nitro-α-phenoxy-propionic acid N-(ethoxycarbonylmethyl)amide.

8. Herbicidal composition comprising an agriculturally acceptable carrier and, in effective amounts, a phenoxycarboxylic acid amide compound as claimed in claim 1.

9. Herbicidal composition as claimed in claim 8 containing from 0.1 to 95% of the active compound by weight.

10. Method of combating weeds, which method comprises applying to an area of cultivation an effective amount of a phenoxycarboxylic acid amide compound as claimed in claim 1.

11. Method as claimed in claim 10 wherein said compound is applied at a dosage of 0.1 to 5 kg per hectare.

12. Method as claimed in claim 10 wherein said compound is applied at a dosage of 0.05 to 10 kg per hectare.

13. Method of combating weeds which method comprises applying to an area of cultivation an effective amount of a compound selected from
5-(2-chloro-4-trifluoromethyl-phenoxy)-2-nitro-α-phenoxy-propionic acid pyrazolide;
5-(2-chloro-4-trifluoromethyl-phenoxy)-2-nitro-α-phenoxy-propionic acid N-(ethoxycarbonylmethyl)amide; and
5-(2,6-dichloro-4-trifluoromethyl-phenoxy)-2-nitro-α-phenoxy-propionic acid N-(ethoxycarbonylmethyl)amide.

* * * * *

UNITED STATES PATENT AND TRADEMARK OFFICE
CERTIFICATE OF CORRECTION

PATENT NO. : 4,500,341

DATED : February 19, 1985

INVENTOR(S) : Heinz Förster, et al.

It is certified that error appears in the above-identified patent and that said Letters Patent is hereby corrected as shown below:

Column 1, line 63 change "akoanoyl" to -- alkanoyl --;

Column 3, line 9 change "Gyperus" to -- Cyperus --;

Claim 1, line 1 change "Phenoxylcarboxylic" to

-- Phenoxycarboxylic --.

Signed and Sealed this

First Day of October 1985

[SEAL]

Attest:

Attesting Officer

DONALD J. QUIGG

Commissioner of Patents and Trademarks—Designate